(12) United States Patent
Venkateswara-Rao

(10) Patent No.: US 10,420,860 B2
(45) Date of Patent: Sep. 24, 2019

(54) COATINGS, MATERIALS, AND DEVICES WITH BIOHEALING PROPERTIES

(71) Applicant: Kondapavulur T. Venkateswara-Rao, San Jose, CA (US)

(72) Inventor: Kondapavulur T. Venkateswara-Rao, San Jose, CA (US)

(*) Notice: Subject to any disclaimer, the term of this patent is extended or adjusted under 35 U.S.C. 154(b) by 0 days.

(21) Appl. No.: 14/992,874

(22) Filed: Jan. 11, 2016

(65) Prior Publication Data

US 2016/0199543 A1    Jul. 14, 2016

Related U.S. Application Data

(60) Provisional application No. 62/101,377, filed on Jan. 9, 2015.

(51) Int. Cl.
| | |
|---|---|
| *A61L 31/08* | (2006.01) |
| *A61L 31/10* | (2006.01) |
| *A61L 31/16* | (2006.01) |
| *A61L 31/12* | (2006.01) |

(52) U.S. Cl.
CPC ............ *A61L 31/088* (2013.01); *A61L 31/10* (2013.01); *A61L 31/128* (2013.01); *A61L 31/16* (2013.01); *A61L 2300/416* (2013.01); *A61L 2420/04* (2013.01); *A61L 2420/06* (2013.01)

(58) Field of Classification Search
None
See application file for complete search history.

(56) References Cited

U.S. PATENT DOCUMENTS

| | | | |
|---|---|---|---|
| 5,084,491 A * | 1/1992 | Kerby | A61K 6/0023 523/115 |
| 5,679,815 A | 10/1997 | Kirlin et al. | |
| 6,099,561 A | 8/2000 | Alt | |
| 6,478,815 B1 | 11/2002 | Alt | |
| 6,702,849 B1 | 3/2004 | Dutta et al. | |
| 8,802,184 B2 | 8/2014 | Hossainy | |
| 2005/0124976 A1 * | 6/2005 | Devens, Jr. | A61M 25/0045 604/523 |

(Continued)

FOREIGN PATENT DOCUMENTS

WO    WO 2014087414 A1    6/2014

OTHER PUBLICATIONS

PCT application PCT/US2016/012889, dated Apr. 22, 2016 ISR/WO.

(Continued)

*Primary Examiner* — Carlos A Azpuru
*Assistant Examiner* — Casey S Hagopian
(74) *Attorney, Agent, or Firm* — Jinn Su

(57) ABSTRACT

Coatings, materials, and devices with biohealing properties are described. A biohealing coating may include a base material and biohealing particles. The base material may include a polymer. The biohealing particles may include one or more of metal particles, alloy particles, metal oxide particles, carbon particles, carbide particles, and nitride particles. The biohealing coating may be applied to an implantable device. A biohealing material may include a base material in bulk form and biohealing particles. The biohealing material may be used to manufacture an implantable device. An implantable device may include one or both of a biohealing coating and a biohealing material.

6 Claims, 5 Drawing Sheets

(56) References Cited

U.S. PATENT DOCUMENTS

| | | | |
|---|---|---|---|
| 2008/0033522 A1* | 2/2008 | Grewe | A61L 31/082 623/1.11 |
| 2008/0058919 A1* | 3/2008 | Kramer-Brown | A61L 31/08 623/1.34 |
| 2008/0195194 A1 | 8/2008 | Pacetti et al. | |
| 2009/0118813 A1 | 5/2009 | Scheuermann et al. | |
| 2009/0123521 A1* | 5/2009 | Weber | A61L 27/30 424/426 |
| 2010/0035047 A1* | 2/2010 | Ajayan | C08J 3/20 428/328 |
| 2010/0230517 A1 | 9/2010 | Yadav et al. | |
| 2010/0255447 A1* | 10/2010 | Biris | A61C 8/0013 433/201.1 |
| 2011/0123589 A1* | 5/2011 | Donati | C08B 37/003 424/409 |
| 2013/0129912 A1 | 5/2013 | Cho et al. | |

OTHER PUBLICATIONS

"X-Ray Mass Attenuation Coefficients," National Institute of Standards and Technology, Jul. 12, 2004, https://www.nist.gov/pml/x-ray-mass-attenuation-coefficients.

Gatto et al., Coronary artery disease evolution in bare-metal stent implantation: safety and efficacy of REBEL™ platinum-chromium coronary stent system, Interventional Cardiology, 2014 6(6), 507-514.

Jorge et al., Clinical utility of platinum chromium bare-metal stents in coronary heart disease, Medical Devices: Evidence and Research, 2015:8 359-367.

\* cited by examiner

COATINGS, MATERIALS, AND DEVICES WITH BIOHEALING PROPERTIES

CROSS-REFERENCE TO RELATED APPLICATION

This application claims the benefit of U.S. provisional application No. 62/101,377, filed Jan. 9, 2015, which is hereby incorporated by reference in its entirety.

BACKGROUND

Atherosclerosis, coronary heart disease and peripheral vascular disease are chronic diseases affecting patient mortality around the world. Today, it is estimated that about a million Americans will suffer from a new heart attack every year, and about 500,000 people will have a recurrent attack. Nearly two to three times that many people are affected by this disease around the world. Patients are treated by oral medication, open surgery (such as, coronary artery bypass grafting or CABG) and minimally-invasive endovascular methods (such as, percutaneous transluminal coronary angioplasty or PTCA, percutaneous transluminal angioplasty or PTA).

Percutaneous endovascular intervention is the most frequently performed therapeutic procedure to treat vascular disease using balloon angioplasty and stents. Stents are tubular-shaped devices which hold open a blood vessel or other body lumen (such as a coronary, carotid, iliac, or femoral artery) after delivery and deployment to the target site using a catheter. However, injury to the blood vessel wall from stents may cause neo-intimal hyperplasia, restenosis, and repeat vascularization in a significant number of patients. Drug-eluting stents (DES), with controlled release of antiproliferative or anti-inflammatory agents over time, have reduced the restenosis rates and repeat revascularization rates compared to bare metal stents (BMS). Today, drug-eluting stents are implanted in over 2 million patients per year, worldwide, to treat various forms of cardiovascular and vascular disease.

Though DES have significantly improved the treatment efficacy and reduced repeat revascularizations compared to BMS, their long-term safety is in question. DES have been associated with an increased risk of very late thrombosis beyond one year, and in some cases up to three to five years, after stent implantation. Stent thrombosis is a rare but serious complication that occurs with DES and BMS immediately after stent placement inside the artery. Sub-optimal stent deployment, incomplete stent apposition against the artery wall, inadequate platelet inhibition, chronic inflammation and delayed arterial healing are some factors that cause acute or sub-acute thrombosis within the first six months after stent implantation. In particular, chronic inflammation and delayed healing are more prevalent with DES than BMS, causing higher incidence of late thrombotic events beyond six months.

Similarly, bioresorbable polymeric stents and bioresorbable vascular scaffolds (BVS) currently undergoing clinical evaluation also show higher inflammation, higher risk for thrombosis, and lower biocompatibility compared to BMS and metallic DES. As a result, polymeric stents are also prone to late stent thrombosis beyond six months after stent implantation.

Intense review of clinical trial data by regulatory agencies and professional societies led to the recommendation of extending the dual anti-platelet drug therapy for at least 12 months and in some cases two years after drug-eluting stent implantation to mitigate the risk of thrombosis. The use of prolonged oral antiplatelet therapy may be costly and increased the economic burden on healthcare. More recent reports indicate that, for patients that received a coronary stent, the need for subsequent cardiac and non-cardiac surgery is associated with considerable risk of ischemic and bleeding events due to the prolonged use of dual anti-platelet therapy (DAPT) in the perioperative phase. Stopping DAPT for surgery in stented patients lowers the risk of bleeding but increases the risk of thrombosis and ischemic events. Such prolonged use may also lead to other side effects, especially in patients with other comorbidities. In addition, patients are often non-compliant to daily oral medication which increases their risk for the incidence of clinical adverse events.

What is needed are compositions and materials for making coatings and medical devices with biohealing and biocompatibility properties to reduce the risk of thrombotic events (acute, sub-acute and late), reduce the dependence of patients on DAPT after implanting a medical device, and reduce other adverse clinical events associated with DES and implantable medical devices.

SUMMARY

Compositions for coating an implantable device are described. In one embodiment, a composition may comprise a polymer and one or more of metal particles, alloy particles, metal oxide particles, carbon particles, carbide particles, and nitride particles.

Biohealing materials are described. In one embodiment, a biohealing material may comprise a polymer and one or more of metal particles, alloy particles, metal oxide particles, carbon particles, carbide particles, and nitride particles.

Implantable devices are described. In one embodiment, an implantable device may comprise a substrate and a biohealing coating applied to at least a portion of a surface of the substrate. The biohealing coating may include a polymer and one or more of metal particles, alloy particles, metal oxide particles, carbon particles, carbide particles, and nitride particles. In another embodiment, an implantable device may comprise a biohealing material. The biohealing material may include a polymer and one or more of metal particles, alloy particles, metal oxide particles, carbon particles, carbide particles, and nitride particles.

Methods of improving biohealing properties of an implantable device are described. In one embodiment, a method comprises applying a biohealing coating on the implantable device. The biohealing coating may include a polymer and one or more of metal particles, alloy particles, metal oxide particles, carbon particles, carbide particles, and nitride particles.

Methods of treating a disorder in a patient are described. In one embodiment, a method comprises implanting in the patient an implantable device. The implantable device may have a substrate and a biohealing coating. The biohealing coating may include a polymer and one or more of metal particles, alloy particles, metal oxide particles, carbon particles, carbide particles, and nitride particles. In another embodiment, a method comprises implanting in the patient an implantable device. The implantable device may include a biohealing material. The biohealing material may include a polymer and one or more of metal particles, alloy particles, metal oxide particles, carbon particles, carbide particles, and nitride particles.

BRIEF DESCRIPTION OF THE DRAWINGS

FIG. 1A shows a side view of implantable device 10. FIG. 1B shows a cross-sectional view of implantable device 10.

FIG. 2A shows a cross-sectional view of a portion of implantable device 100. FIG. 2B shows an enlarged view of a surface of implantable device 100.

FIG. 3A shows a cross-sectional view of a portion of implantable device 200. FIG. 3B shows an enlarged view of a surface of implantable device 200.

FIG. 4A shows a cross-sectional view of a portion of implantable device 300. FIG. 4B shows an enlarged view of a surface of implantable device 300.

FIG. 5 shows a cross-sectional view of a portion of implantable device 400.

FIG. 6 shows a cross-sectional view of a portion of implantable device 500.

DESCRIPTION

Coatings, materials, and devices with biohealing properties are described. A biohealing coating may include a base material and biohealing particles. The base material may include a polymer. The biohealing particles may include one or more of metal particles, alloy particles, metal oxide particles, carbon particles, carbide particles, and nitride particles. The biohealing coating may be applied to an implantable device. A biohealing material may be a composite material which includes a base material in bulk form and biohealing particles interdispersed in the base material. The biohealing material may be used to manufacture an implantable device. An implantable device may include one or both of a biohealing coating and a biohealing material.

The coatings, materials, and devices described may provide one or more of improved biohealing, improved biocompatibility, reduced thrombogenicity, reduced endothelialization time, reduced fibrin deposition, reduced injury, reduced inflammation, reduced platelet adhesion, reduced risk of thrombosis, reduced risk of late thrombosis, enhanced arterial healing, and reduced likelihood of adverse clinical events.

Figure 1A:
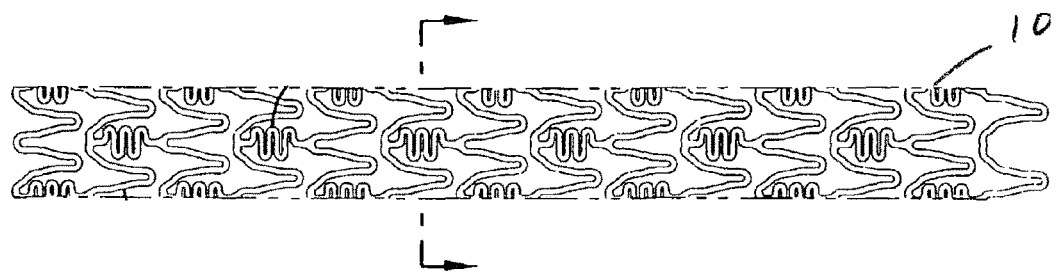
FIGS. 1A-1B show one embodiment of an implantable device 10.
Figure 1B:
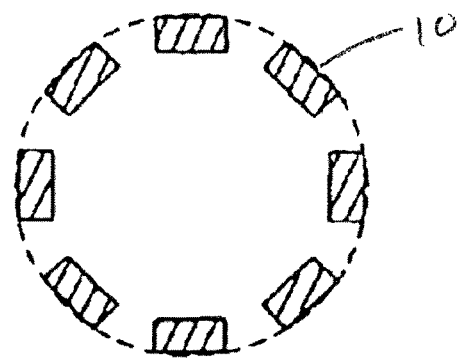

FIGS. 1A-1B show one embodiment of an implantable device 10. FIG. 1A shows a side view of implantable device 10. FIG. 1B shows a cross-sectional view of implantable device 10.

Implantable device 10 may be configured to be placed in a blood vessel, organ, or any other part of the body.

Figure 2A:
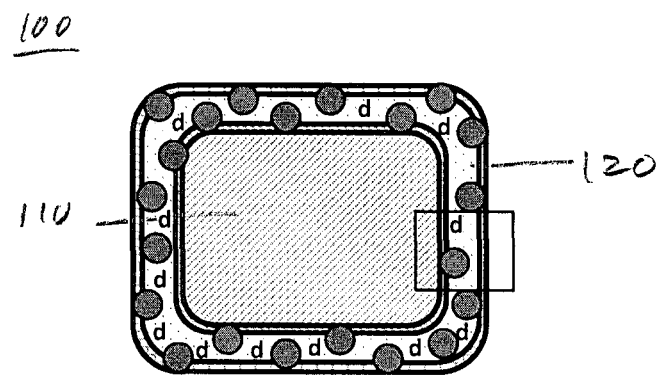
FIGS. 2A-2B show another embodiment of an implantable device 100.
Figure 2B:
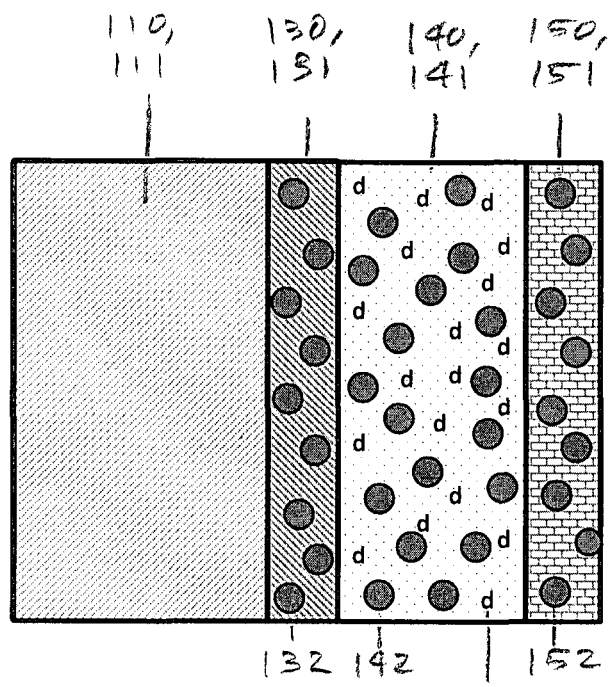

FIGS. 2A-2B show another embodiment of an implantable device 100. FIG. 2A shows a cross-sectional view of a portion of implantable device 100. FIG. 2B shows an enlarged view of a surface of implantable device 100.

Implantable device 100 may be configured to be placed in a blood vessel, organ, or any other part of the body.

Implantable device 100 may include a substrate 110.

Substrate 110 may include a base material 111. Base material 111 may include a metallic material. Base material 111 may include one or more of a ceramic, intermetallic, composite, or any other suitable material.

Implantable device 100 may include a biohealing coating 120. Biohealing coating 120 may be applied to at least a portion of substrate 110.

Biohealing coating 120 may include one or more layers.

Biohealing coating 120 may include a first layer 130. First layer 130 may be a primer layer. First layer 130 may be configured to prime a surface of substrate 110 to promote good coating adhesion. First layer 130 may include a base material 131. Base material 131 may include a polymer or any other suitable material. First layer 130 may include biohealing particles 132. Biohealing particles 132 may be distributed uniformly or non-uniformly in base material 131.

Biohealing coating 120 may include a second layer 140. Second layer 140 may be a drug reservoir layer. Second layer 140 may be configured to hold at least one drug 143. Second layer 140 may include a base material 141. Base material 141 may include a polymer or any other suitable material. Second layer 140 may include biohealing particles 142. Biohealing particles 142 may be distributed uniformly or non-uniformly in base material 141. Drug 143 may be distributed uniformly or non-uniformly in base material 141.

Biohealing coating 120 may include a third layer 150. Third layer 150 may be a barrier layer. Third layer 150 may be a membrane with pores. Third layer 150 may be configured to control release of drug 143 over time after implantable device 100 has been placed in the body. Third layer 150 may include a base material 151. Base material 151 may include a polymer or any other suitable material. Third layer 150 may include biohealing particles 152. Biohealing particles 152 may be distributed uniformly or non-uniformly in base material 151.

One or more of biohealing particles 132, 142, and 152 may include one or more of metal particles, alloy particles, metal oxide particles, carbon particles, carbide particles, and nitride particles.

One or more of biohealing particles 132, 142, and 152 may make up a volume fraction of each of first layer 130, second layer 140, and third layer 150, respectively, of approximately 0.01 to 20%.

One or more of biohealing particles 132, 142, and 152 may have a particle size of approximately 0.01 to 10,000 nm, or approximately 100 to 5000 nm.

One or more of biohealing particles 132, 142, and 152 may be sphere-shaped, cube-shaped, irregular-shaped, or any other suitable shape.

One or more of biohealing particles 132, 142, and 152 may be configured to reduce their effect on polymer cross-linking, polymer structure, mechanical properties, and other functional properties of base material 131, 141, and 151.

One or more of biohealing particles 132, 142, and 152 may be configured to reduce their effect on degradation profile, coating process, and coating performance of biohealing coating 120.

One or more of biohealing particles 132, 142, and 152 may be configured to reduce their loss into the blood stream or body to levels at or below acceptable levels for metallic implants. One or more of biohealing particles 132, 142, and 152 may be configured to reduce the likelihood of large embolic debris. One or more of biohealing particles 132, 142, and 152 may be configured for ease of manufacturing, such as by reducing clustering and interactions with drug, solvent, and polymer molecules.

Biohealing coating 120 may be configured to release drug 143 into the body over time. Biohealing coating 120 may be configured to release drug 143 into the body over one to six months or longer. Third layer 150 may be configured to control the release of drug 143 into the body over time by selecting base material 151 with suitable drug permeability, such as a polymer with suitable pore size and/or pore density.

One or more of biohealing particles 132, 142, and 152 may be configured to reduce their effect on drug-release kinetics, drug uptake into tissue, and drug efficacy.

Figure 3A:
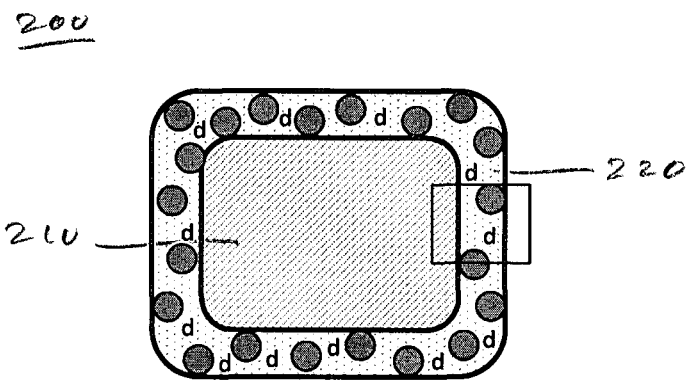
FIGS. 3A-3B show another embodiment of an implantable device 200.
Figure 3B:
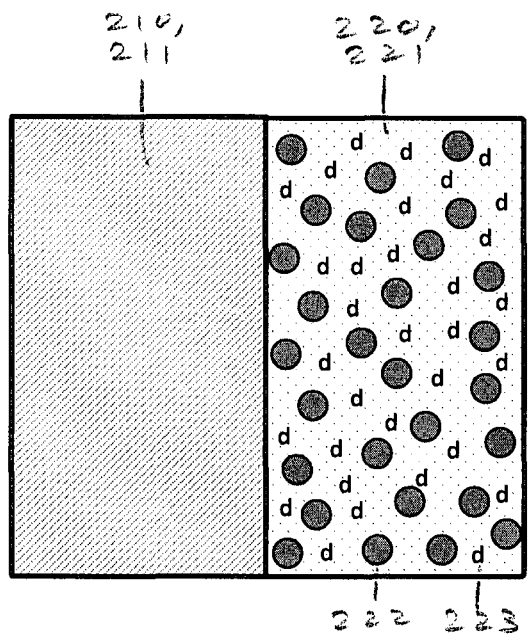

FIGS. 3A-3B show another embodiment of an implantable device 200. FIG. 3A shows a cross-sectional view of a portion of implantable device 200. FIG. 3B shows an enlarged view of a surface of implantable device 200.

Implantable device 200 may be configured to be placed in a blood vessel, organ, or any other part of the body.

Implantable device 200 may include a substrate 210.

Substrate 210 may include a base material 211. Base material 211 may include a metallic material. Base material 211 may include one or more of a ceramic, intermetallic, composite, or any other suitable material.

Implantable device 200 may include a biohealing coating 220. Biohealing coating 220 may be applied to at least a portion of substrate 210.

Biohealing coating 220 may include a base material 221. Biohealing coating 220 may include a polymer or any other suitable material.

Biohealing coating 220 may include biohealing particles 222. Biohealing particles 222 may be distributed uniformly or non-uniformly in base material 221. Biohealing particles 222 may include one or more of metal particles, alloy particles, metal oxide particles, carbon particles, carbide particles, and nitride particles.

Biohealing particles 222 may make up a volume fraction of biohealing coating 220 of approximately 0.01 to 20%.

Biohealing particles 222 may have a particle size of approximately 0.01 to 10,000 nm, or approximately 100 to 5000 nm.

Biohealing particles 222 may be sphere-shaped, cube-shaped, irregular-shaped, or any other suitable shape.

Biohealing particles 222 may be configured to reduce their effect on polymer cross-linking, polymer structure, mechanical properties, and other functional properties of base material 221.

Biohealing particles 222 may be configured to reduce their effect on degradation profile, coating process, and coating performance of biohealing coating 220.

Biohealing particles 222 may be configured to reduce their loss into the blood stream or body to levels at or below acceptable levels for metallic implants. Biohealing particles 222 may be configured to reduce the likelihood of large embolic debris. Biohealing particles 222 may be configured for ease of manufacturing, such as by reducing clustering and interactions with drug, solvent, and polymer molecules.

Biohealing coating 220 may include a drug 223. Drug 223 may be distributed uniformly or non-uniformly in base material 221.

Biohealing coating 220 may be configured to release drug 223 into the body over time. Biohealing coating 220 may be configured to release drug 223 into the body over one to six months or longer. Base material 221 that includes a biostable polymer may be configured to elute drug 223 into the body over time. Base material 221 that includes a biostable polymer may include biohealing particles 222 which remain in the polymer after drug 223 has been released into the body. Base material 221 that includes a biodegradable or bioresorbable polymer may be configured to control the release of drug 223 into the body over time by selecting a polymer with suitable degradation characteristics.

Biohealing particles 222 may be configured to reduce their effect on drug-release kinetics, drug uptake into tissue, and drug efficacy.

Figure 4A:
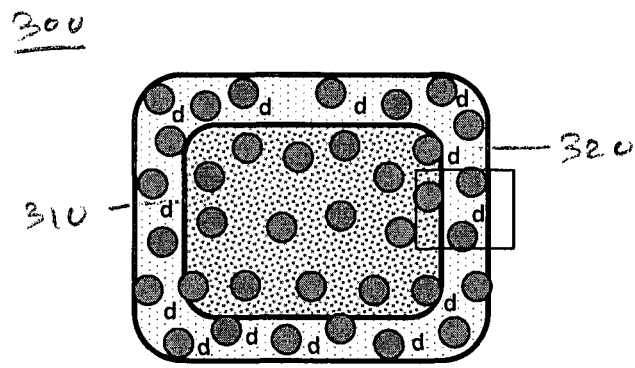
FIGS. 4A-4B show another embodiment of an implantable device 300.
Figure 4B:
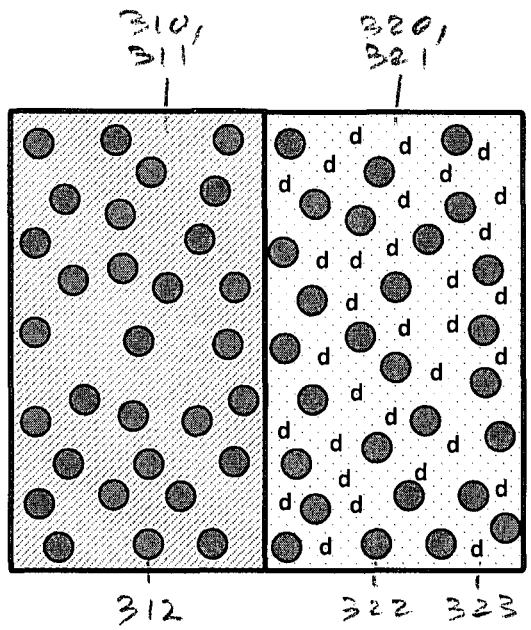

FIGS. 4A-4B show another embodiment of an implantable device 300. FIG. 4A shows a cross-sectional view of a portion of implantable device 300. FIG. 4B shows an enlarged view of a surface of implantable device 300.

Implantable device 300 may be configured to be placed in a blood vessel, organ, or any other part of the body.

Implantable device 300 may include a biohealing material 310.

Biohealing material 310 may include a base material 311. Base material 311 may include a non-metallic material. Base material 311 may include a polymer. Base material 311 may include one or more of a ceramic, intermetallic, composite, or any other suitable material.

Biohealing material 310 may include biohealing particles 312. Biohealing particles 312 may be distributed uniformly or non-uniformly in base material 311. Biohealing particles 312 may include one or more of metal particles, alloy particles, metal oxide particles, carbon particles, carbide particles, and nitride particles.

Biohealing particles 312 may make up a volume fraction of biohealing material 310 of approximately 0.01 to 20%.

Biohealing particles 312 may have a particle size of approximately 0.01 to 10,000 nm, or approximately 100 to 5000 nm.

Implantable device 300 may include a biohealing coating 320. Biohealing coating 320 may be applied to at least a portion of biohealing material 310.

Biohealing coating 320 may include a base material 321. Biohealing coating 320 may include a polymer or any other suitable material.

Biohealing coating 320 may include biohealing particles 322. Biohealing particles 322 may be distributed uniformly or non-uniformly in base material 321. Biohealing particles 322 may include one or more of metal particles, alloy particles, metal oxide particles, carbon particles, carbide particles, and nitride particles.

Biohealing particles 322 may make up a volume fraction of biohealing coating 320 of approximately 0.01 to 20%.

Biohealing particles 322 may have a particle size of approximately 0.01 to 10,000 nm, or approximately 100 to 5000 nm.

Biohealing particles 312 and/or 322 may be sphere-shaped, cube-shaped, irregular-shaped, or any other suitable shape.

Biohealing particles 312 and/or 322 may be configured to reduce their effect on polymer cross-linking, polymer structure, mechanical properties, and other functional properties of base material 311 and/or 321.

Biohealing particles 322 may be configured to reduce their effect on degradation profile, coating process, and coating performance of biohealing coating 320.

Biohealing particles 312 and/or 322 may be configured to reduce their loss into the blood stream or body to levels at or below acceptable levels for metallic implants. Biohealing particles 312 and/or 322 may be configured to reduce the likelihood of large embolic debris. Biohealing particles 312 and/or 322 may be configured for ease of manufacturing, such as by reducing clustering and interactions with drug, solvent, and polymer molecules.

Biohealing coating 320 may include a drug 323. Drug 323 may be distributed uniformly or non-uniformly in base material 321.

Biohealing coating 320 may be configured to release drug 323 into the body over time. Biohealing coating 320 may be configured to release drug 323 into the body over one to six months or longer. Base material 321 that includes a biostable polymer may be configured to elute drug 323 into the body over time. Base material 321 that includes a biostable polymer may include biohealing particles 322 which remain in the polymer after drug 323 has been released into the body. Base material 321 that includes a biodegradable or bioresorbable polymer may be configured to control the release of drug 323 into the body over time by selecting a polymer with suitable degradation characteristics.

Biohealing particles 322 may be configured to reduce their effect on drug-release kinetics, drug uptake into tissue, and drug efficacy.

Figure 5:
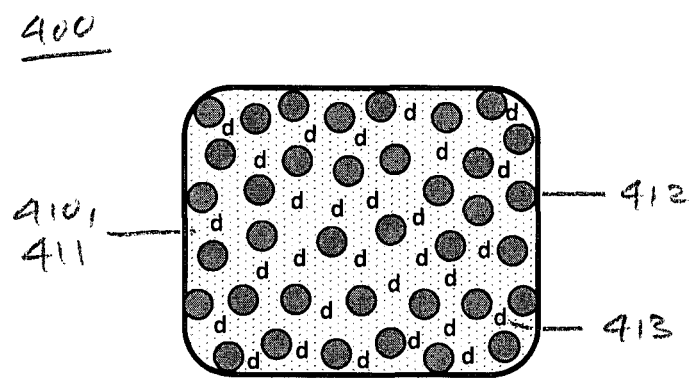
FIG. 5 shows another embodiment of an implantable device 400.

FIG. 5 shows another embodiment of an implantable device 400. FIG. 5 shows a cross-sectional view of a portion of implantable device 400.

Implantable device 400 may be configured to be placed in a blood vessel, organ, or any other part of the body.

Implantable device 400 may include a biohealing material 410.

Biohealing material 410 may include a base material 411. Base material 411 may include a non-metallic material. Base material 411 may include a polymer. Base material 411 may include one or more of a ceramic, intermetallic, composite, or any other suitable material.

Biohealing material 410 may include biohealing particles 412. Biohealing particles 412 may be distributed uniformly or non-uniformly in base material 411. Biohealing particles 412 may include one or more of metal particles, alloy particles, metal oxide particles, carbon particles, carbide particles, and nitride particles.

Biohealing particles 412 may make up a volume fraction of biohealing material 410 of approximately 0.01 to 20%.

Biohealing particles 412 may have a particle size of approximately 0.01 to 10,000 nm, or approximately 100 to 5000 nm.

Biohealing particles 412 may be sphere-shaped, cube-shaped, irregular-shaped, or any other suitable shape.

Biohealing particles 412 may be configured to reduce their effect on polymer cross-linking, polymer structure, mechanical properties, and other functional properties of base material 411.

Biohealing particles 412 may be configured to reduce their loss into the blood stream or body to levels at or below acceptable levels for metallic implants. Biohealing particles 412 may be configured to reduce the likelihood of large embolic debris. Biohealing particles 412 may be configured for ease of manufacturing, such as by reducing clustering and interactions with drug, solvent, and polymer molecules.

Biohealing material 410 may include a drug 413. Drug 413 may be distributed uniformly or non-uniformly in base material 411.

Biohealing material 410 may be configured to release drug 413 into the body over time. Biohealing material 410 may be configured to release drug 413 into the body over one to six months or longer. Base material 411 that includes a biostable polymer may be configured to elute drug 413 into the body over time. Base material 411 that includes a biostable polymer may include biohealing particles 412 which remain in the polymer after drug 413 has been released into the body. Base material 411 that includes a biodegradable or bioresorbable polymer may be configured to control the release of drug 413 into the body over time by selecting a polymer with suitable degradation characteristics.

Biohealing particles 412 may be configured to reduce their effect on drug-release kinetics, drug uptake into tissue, and drug efficacy.

Figure 6:
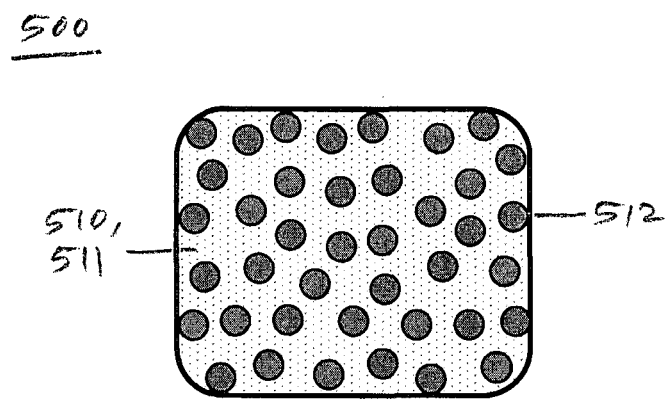
FIG. 6 shows another embodiment of an implantable device 500.

FIG. 6 shows another embodiment of an implantable device 500. FIG. 6 shows a cross-sectional view of a portion of implantable device 500.

Implantable device 500 may be configured to be placed in a blood vessel, organ, or any other part of the body.

Implantable device 500 may include a biohealing material 510.

Biohealing material 510 may include a base material 511. Base material 511 may include a non-metallic material. Base material 511 may include a polymer. Base material 511 may include one or more of a ceramic, intermetallic, composite, or any other suitable material.

Biohealing material 510 may include biohealing particles 512. Biohealing particles 512 may be distributed uniformly or non-uniformly in base material 511. Biohealing particles 512 may include one or more of metal particles, alloy particles, metal oxide particles, carbon particles, carbide particles, and nitride particles.

Biohealing particles 512 may make up a volume fraction of biohealing material 510 of approximately 0.01 to 20%.

Biohealing particles 512 may have a particle size of approximately 0.01 to 10,000 nm, or approximately 100 to 5000 nm.

Biohealing particles 512 may be sphere-shaped, cube-shaped, irregular-shaped, or any other suitable shape.

Biohealing particles 512 may be configured to reduce their effect on polymer cross-linking, polymer structure, mechanical properties, and other functional properties of base material 511.

Biohealing particles 512 may be configured to reduce their loss into the blood stream or body to levels at or below acceptable levels for metallic implants. Biohealing particles 512 may be configured to reduce the likelihood of large embolic debris. Biohealing particles 512 may be configured for ease of manufacturing, such as by reducing clustering and interactions with drug, solvent, and polymer molecules.

An implantable device may include a stent, drug-eluting stent, covered stent, stent-graft, vascular graft, vascular scaffold, heart valve housing, heart valve leaflet, left-ventricular assist device (LVAD), blood pump, endoprosthesis, or any other device configured to be placed at least partially in the body.

A metallic material may include one or more of stainless steel, chromium-cobalt alloy, titanium-nickel alloy, chromium-platinum alloy, tantalum, tantalum alloy, magnesium, magnesium alloy, platinum, platinum alloy, titanium, titanium alloy, niobium, niobium alloy, gold, gold alloy, and any other suitable metallic material.

A polymer may include one or more of a biostable, biodegradable, and bioresorbable polymer. A polymer may include one or more of a homopolymer, copolymer, graft polymer, block polymer, polymer with special functional or end groups such as acidic or hydrophilic type, and blend of two or more homopolymers or copolymers.

A polymer may include one or more of a polyanhydride, polyamide, polyurea, polyether, polyalkylene carbonate, polyacrylic acid, polyamine, polyester amide, polyester amine, polyvinylacetate, polyethylene imine, polycyanoacrylate, polyphosphazene, polyphosphate, polyphosphonate, polysulfonate, polysulfonamide, polylactide, polyglycolide, regenerated cellulose, and biopolymer or blend.

A polymer may include one or more of poly-n-butyl methacrylate (PBMA), polyethylene-co-vinyl acetate (PEVA), poly-styrene-b-isobutylene-styrene (PIBS, a polyolefin derivative), vinylidene fluoride (VDF) and hexafluoropropylene (HFP) fluoropolymers, polyethylene glycol (PEG), phosphorlycholine (PC), expanded polytetrafluoroethylene (e-PTFE), polytetrafluoroethylene (PTFE), polyester (Dacron), polyurethane, polyester, and poly methylmethacrylate (PMMA).

A polymer may include one or more of poly caprolactone (PCL), poly lactic acid (PLA), poly-L-lactic acid (PLLA), poly-D-lactic acid (PDLA), poly-L-lactic-glycolic acid (PLGA), poly-glycolic acid (PGA), poly(alkene carbonate), polyethylene carbonate (PEC), and copolymers of poly (lactide) and trimethylene carbonate (TMC), copolymers of poly(lactide) and poly(glycolide), copolymers of poly(lactide) polyethylene glycol (PEG) family of polymers, poly (L-lactic acid), poly(L/D-lactic acid), poly(L/DL-lactic acid), poly(glycolic acid), poly(lactide-co-glycolide), polydioxanone, poly(ethyl glutamate), poly(hydroxybutyrate), polyhydroxyvalerate, poly(3-hydroxybutyrate-co-hydroxyvalerate), polycaprolactone, poly(ether esters), poly(trimethylcarbonate), poly(L-lactic acid-co-trimethylene carbonate), poly(L/D-lactic acid-co-trimethylene carbonate), poly(L/DL-lactic acid-co-trimethylene carbonate), poly(caprolactone-co-trimethylene carbonate), poly(glycolic acid-co-trimethylene carbonate), poly(glycolic acid-co-trimethylene carbonate-co-dioxanone), polyethylene carbonate, poly(trimethylene carbonate), polypropylene carbonate, poly(iminocarbonates), poly(malic acid), modified poly(ethylene terephthalate), poly(butylene succinate), poly(butylene succinate adipate), poly(butylene succinate terephthalate), poly (butylene adipate-co terephthalate), starch based polymers, hyaluronic acid, oxidized or non-oxidized regenerated cellulose copolymers and other aliphatic polyesters, and suitable copolymers thereof.

A polymer may include one or more of poly (L-lactide), poly (D,L-lactide), poly (glycolide), 50-50% poly D,L-lactide/glycolide, X-Y poly D,L-lactide/glycolide, where X=0.1-99.9% and (Y=100-X) %, 82-18% poly L-lactide/glycolide, X-Y poly L-lactide/glycolide, where X=0.1-99.9% and (Y=100-X) %, 70/30 poly L-lactide/ε-caprolactone, X-Y poly L-lactide/ε-caprolactone, where X=0.1-99.9% and (Y=100-X) %, and 85-15% poly(L-lactide-co-glycolide). A polymer may include one or more of poly-(L-lactide, D-lactide, DL-lactide) and PLDA, and their copolymers. The crystallinity of a polymer may be controlled by subsequent thermal treatments at different temperatures.

Metal and metal oxide particles may include one or more of chromium (Cr), chromium oxide ($Cr_2O_3$, CrO, $CrO_2$, $CrO_3$, $CrO_5$), titanium (Ti), titanium oxide (TiO, $TiO_2$, $Ti_2O_3$), tantalum (Ta), tantalum pentoxide ($Ta_2O_5$), platinum (Pt), platinum oxide (PtO, $PtO_2$), palladium (Pd), palladium oxide (PdO), gold (Au), gold oxide ($Au_2O_3$), niobium (Nb), niobium oxide (NbO, $NbO_2$, $Nb_2O_5$), vanadium (V), vanadium oxide (VO, $VO_2$, $V_2O_3$, $V_2O_5$), molybdenum (Mo), molybdenum oxide ($MoO_2$, $MoO_3$), manganese (Mn), manganese oxide (MnO, $MnO_2$, $Mn_2O_3$, $Mn_3O_4$, $Mn_2O_7$), tungsten (W), tungsten oxide ($WO_2$, $W_2O_3$), iron (Fe), iron oxide (FeO, $Fe_2O_3$), rhodium (Rh), rhodium oxide ($RhO_2$, $Rh_2O_3$), cobalt (Co), cobalt oxide (CoO, $Co_2O_3$, $Co_3O_4$), iridium (Ir), iridium oxide (IrOx), magnesium (Mg), magnesium oxide (MgO), zirconium (Zr), zirconium oxide ($ZrO_2$), ruthenium (Ru), ruthenium oxide ($RuO_2$, $RuO_4$), hafnium (Hf), hafnium oxide ($HfO_2$), rhenium (Re), and rhenium oxide ($ReO_2$, $ReO_3$, $Re_2O_7$).

Alloy particles may include one or more of stainless steel (316, 316L, 316 LS, 316 LVM, 304, Pt-SS, BioDur 108 Ni-free SS, Biodur 734 SS alloy, 475 SS), chromium-cobalt alloy (L605, MP35N, MP35N-Low Ti, Elgiloy, Biodur Carpenter CCM Cr—Co—Mo Alloy, Biodur CCM Plus Cr—Co—Mo alloy, Conichrome), titanium alloy (Ti-6Al-4V ELI, CP Titanium Grades 1, 2 and 4, Ti-6Al-7Nb), titanium-nickel alloy (SE 508, Ni+(48-52 at %)Ti alloys), chromium-platinum alloy (Synergy alloy by Boston Scientific), platinum-palladium alloys, platinum-iridium alloys, niobium-based alloys, and iron-based alloys (steels).

Carbon particles may include one or more of graphitic form, nanotubes, nanospheres, pyrolitic carbon, diamond, or any other suitable form.

Carbide particles include one or more of calcium carbide ($CaC_2$) silicon carbide (SiC), boron carbide ($B_4C$, $B_{25}C$), cementite ($Fe_3C$), magnesium carbide ($Mg_2C$), titanium carbide (TiC), zirconium carbide (ZrC), hafnium carbide (HfC), vanadium carbide (VC, $V_2C$ and $V_4C_3$), niobium carbide (NbC, $Nb_2C$ and $Nb_4C3$), tantalum carbide (TaC, $Ta_2C$, $Ta_4C_3$), chromium carbide ($Cr_{23}C_6$, $Cr_3C$, $Cr_7C_3$, $Cr_3C_2$), molybdenum carbide ($Mo_2C$, $Mo_3C_2$) and tungsten carbide (WC, $W_2C$).

Nitride particles may include one or more of silicon nitride ($Si_3N_4$), titanium nitride (TiN), boron nitride (BN), magnesium nitride ($Mg_3N_2$), calcium nitride ($Ca_3N_2$), zirconium nitride (ZrN), tungsten nitride (WN, $W_2N$, $WN_2$), vanadium nitride (VN, $V_2N$), tantalum nitride (TaN) and niobium nitride (NbN).

A drug may include an immunosuppressive drug, such as one or more of sirolimus, everolimus, biolimus, novolimus, and zotarolimus.

A drug may include an antiproliferative drug, such as paclitaxel.

A drug may include one or more of anti-inflammatory, anti-thrombotic, immunomodulating, anti-cancer, anti-platelet, antifungal, antidiabetic, antihyperlipidemia, antiangiogenic, angiogenic, and antihypertensive drugs.

A drug may include one or more of AP20840, AP23841, AP23573, CCI-779, deuterated rapamycin, TAFA93, tacrolimus, cyclosporine, TKB662, myriocin, neuromodulatory drugs, non-steroidal anti-inflammatory drugs (NSAIDs), and their analogues, prodrugs, derivatives, metabolites, fragments, precursors, and salts.

One embodiment of a method for manufacturing a biohealing coating may include mixing biohealing particles with one or more of a polymer, solvent, additive (such as a plasticizer and/or stabilizer), drug, and excipient.

A biohealing coating may be applied to an implantable device using any suitable method. The biohealing coating may be applied by ultrasonic spray coating (such as with a MediCoat DES 3000 available from Sonotek Corp., Milton, N.Y.), and/or ink-jet coating (such as with an ink-jet microdispenser available from MicroFab Technologies, Plano, Tex.). Dual or multiple nozzle configurations are available for layering different chemistries or mixing spray solutions. In one process embodiment, a first spray nozzle may be used to spray coat a drug and polymer solution, while a second spray nozzle may be used to spray coat biohealing particles at a predetermined rate to achieve a desired volume fraction and uniform particle dispersion, either simultaneously or alternatingly. Such a dual-spray coating process may help uniformity of particle dispersion within the coating, prevent particle clustering and limit drug-particle interactions during mixing, storage, and spraying. This process may be used to create multilayer coatings, with different polymer/biohealing particles/drug and additive ratios in each layer. For example, a first or inner layer may have a lower concentration of biohealing particles, while a second or outer layer may have a higher concentration of biohealing particles.

A biohealing coating may be applied using techniques used to deposit thin metallic films on non-metallic substrates, such as one or more of micro-contact printing, nanotransfer printing and sol-gel processing.

A biohealing coating may be applied using three-dimensional (3D) printing techniques.

A biohealing coating may be applied by one or more of dip coating (by repeated immersion and drying), painting (air brush or manual), and deposition (manual or automated) using syringes and/or pipettes. The implantable device may be rotated to achieve a uniform coating on the implantable device surface with the desired drug load, drug release profile, coating integrity, and coating thickness. The coated implantable device may then be dried or evaporated to release solvents.

A biohealing coating may be applied to all or selected surfaces of an implantable device. For example, the biohealing coating may be applied only to the outer surfaces or blood-contacting surfaces of an implantable device. As another example, for an implantable device that is an intraluminal device such as a stent, the biohealing coating may be applied only along the abluminal surfaces (in direct contact with the blood vessel surface). This may be done by masking the luminal and cross-sectional (wall) surfaces of the intraluminal device. For a metallic stent with struts having a rectangular cross section, this may preserve the metallic surface on three of the four sides, while the biohealing coating is applied to only one of the four sides, the side in contact with the blood vessel.

One embodiment of a method for manufacturing a biohealing material may include mixing biohealing particles with one or more of a polymer (in pellet or powder form), solvent, additive (such as a plasticizer and/or stabilizer), drug, and excipient.

A biohealing material may be fabricated into an implantable device using any suitable method. A biohealing material may be extruded into hollow cylindrical tubes or hypotubes, which may be used to fabricate expandable tubular structures such as stents. Extrusion temperatures may be selected to prevent degradation of the polymer and drug, while high enough to achieve a homogenous extrusion with a desired distribution of biohealing particles. The biohealing material (in tubular or solid form) may be laser cut to obtain a desired shape or pattern for the implantable device. A biohealing material may be molded, such as by injection molding, into a desired form in a die, such as an expandable stent. A biohealing material may be sprayed and/or dipped onto a mandrel into a desired form. For example, a hypotube of the biohealing material may be fabricated by coating a cylindrical mandrel, drying the coated mandrel in an oven, and then separating the hypotube from the mandrel. The biohealing material may be subjected to various heat treatments (such as annealing and/or quenching) to achieve desired structural and mechanical properties. Processing parameters may be optimized to reduce the degradation of a polymer and/or drug and maintain treatment efficacy of the implantable device.

A biohealing material may be printed using three-dimensional (3D) printing techniques into a desired form. A 3D printer may deposit solid beads of the biohealing material in two dimensions (X, Y). The 3D printer may then deposit the beads layer by layer in a third dimension (Z), utilizing the previous layer for support. Using this method, different materials may be deposited, including support material (to be dissolved away afterwards) as well as various polymers with different concentrations of biohealing particles, additives, drugs, and excipients.

In addition to improving the biohealing characteristics of implantable devices, the addition of biohealing particles that are one or more of metal particles, alloy particles, metal oxide particles, carbon particles, carbide particles, and nitride particles may also enhance the strength of the implantable device. For example, the radial strength of tubular structures such as stents may be increased due to reinforcement of the polymer (low modulus) by one or more of metal particles, alloy particles, and metal oxide particles (high modulus). Secondly, metal particles, alloy particles, metal oxide particles, carbide particles, and nitride particles may also enhance the visibility of polymeric devices under X-ray fluoroscopy due to the higher X-ray absorption coefficient of metal particles, alloy particles, and metal oxide particles. Thirdly, metal particles, alloy particles, metal oxide particles, carbide particles, and nitride particles may also improve the crystallinity of polymers used to fabricate implantable devices. Higher crystallinity may improve the strength of the polymer and reduce or control the in vivo degradation time of the polymeric device. Metal particles, alloy particles, metal oxide particles, carbide particles, and nitride particles may alter the heat conduction properties of the polymer and control the crystallinity during polymer processing and subsequent heat treatments.

Example 1

Drug-eluting stents may be fabricated by laser-cutting and electropolishing L605 cobalt-chromium alloy hypotubes to form a bare metallic stent structure. These metal stent may be coated with an vinylidene fluoride+hexafluoropropylene (VDF+HFP) copolymer containing approximately 5 wt. % (mass fraction=0.05) of L605 cobalt-chromium alloy particles and containing 90 micrograms of everolimus drug (to yield a drug concentration of 5 microgram/mm) on an 18 mm long stent, as a single layer with a biohealing coating thickness of approximately 8 microns.

Alternatively, these stents may be spray coated with a first layer of VDF+HFP copolymer containing approximately 5 wt. % stainless steel particles to yield a thickness of approximately 0.5-1 microns; followed by spray coating a second layer of VDF+HFP copolymer containing approximately 5 wt. % of stainless steel particles and 90 micrograms of everolimus drug (on an 18 mm long stent), of approximately 2-6 microns in thickness; and a final layer of VDF+HFP copolymer+stainless steel particles, of approximately 1-2 microns in thickness.

Alternatively, sirolimus (150 micrograms on an 18 mm long stent), biolimus, zotarolimus (180 micrograms on a 18 mm long stent) and paclitaxel drugs of equivalent concentrations may also be used in place of the everolimus drug. PBMA, PLA and PC, PLGA polymers mixed with biohealing particles may also be used as the material for a biohealing coating. Equivalent amounts of one or more of titanium, titanium oxide, and chromium oxide particles may be used as the biohealing particles.

Example 2

Polymeric hypotubes or wires may be formed by extruding PLA pellets mixed with approximately 5 wt. % (mass fraction=0.05) of stainless steel powder. Stents may be fabricated by laser-cutting the hollow composite tubes of PLA polymer containing stainless steel. These stents may then be coated with a PLA polymer containing approximately 5 wt. % of stainless steel particles+108 micrograms of everolimus drug (6 microgram/mm) on an 18 mm long stent, as a single coating layer with a thickness of approximately 8-10 microns.

Composite polymeric stents may also be fabricated by weaving the wire forms into a circular mesh to form stents. These stents may then be coated with a PLA polymer containing approximately 5 wt. % of stainless steel particles+108 micrograms of everolimus drug (6 microgram/mm) on an 18 mm long stent, as a single coating layer with a thickness of approximately 8-10 microns.

Composite polymeric stents may also be fabricated by preshaping the wire forms into sinusoidal rings, approximately 2 mm long, and welding the rings together to form a long stent. These stents may then be coated with a PLA polymer containing approximately 5 wt. % of stainless steel particles+108 micrograms of everolimus drug (6 microgram/mm) to make an 18 mm long stent, as a single coating layer with a thickness of approximately 8-10 microns.

Example 3

Drug-eluting stents may be fabricated by laser-cutting and electropolishing cobalt-chromium alloy hypotubes or wire forms. These stents may be coated with a 1 micron layer of phosphorylcholine (PC) containing approximately 5 wt. % (mass fraction=0.05) of cobalt-chromium biohealing particles. A second layer, containing 90% zotarolimus (10 microgram/mm, 180 micrograms on a 18 mm long stent)+ 9.5% PC+0.5% cobalt-chromium particles, may be sprayed to a thickness of approximately 2-3 microns. A third layer of PC+0.5% cobalt-chromium alloy particles, approximately 0.1 microns thick may be sprayed.

Other drugs such as sirolimus, biolimus, everolimus, and paclitaxel of equivalent concentrations may be used. VDF+ HFP, PBMA, PLA, and PLGA polymers may also be used as coating materials. Equivalent amounts of one or more of stainless steel, chromium oxide, and titanium oxide biohealing particles may be used.

Example 4

In-vivo corrosion potentials ≥−100 mV (vs. standard calumel electrode or SCE) and breakdown potentials 300 mV (vs. SCE) are considered acceptable for clinical use of metallic implants inside the body. The acceptable corrosion rates are ≤9500 ng/cm²/day. Accelerated corrosion tests on polished and passivated stainless-steel stent surfaces, per ASTM Standard G5-94, show that the average corrosion potential is >200 mV (vs. SCE) and the average breakdown potential for the oxide coating on the surface is >1000 mV (vs. SCE) suggesting good corrosion resistance inside the body. The average corrosion current for stainless steel stent surfaces is between 44-46 nA/cm², yielding an estimated average mass-loss rate of 980-1027 ng/cm²/day, or a corrosion rate between 0.45-1.11 microns/year.

Stent Surface Area Calculations:

Assuming an average stent diameter of 3.0 mm (D=0.3 cm), stent length of 20 mm (L=2 cm) and a 20% metal-to-artery ratio (metal area fraction $A_f=0.2$), the inner and outer stent surface area may be calculated as: $A1=2\pi DLA_f$, yielding a surface area of about 0.754 cm². Assuming a stent strut thickness of 80 microns (t=80×10⁻⁴ cm) and about 10 rings (n=10) per stent, the cross-sectional wall surface area is estimated as: $A2=2\pi Dnt$, yielding about 0.15 cm². The total stent surface area (A=A1+A2) is about 0.9 cm² for a 20 mm long stent.

Metal Particle Volume Fraction Calculations:

Using 1000 ng/cm²/day as the corrosion rate ($C_R$) for medical grade stainless steel, the amount of corrosion particles (metal degradation products) lost into the body or blood stream is estimated as: $M=AC_R$, yielding 900 ng/day. Assuming a total degradation time of 60 days for a biodegradable drug-eluting coating, the total oxide content (or degradation products) lost into the blood stream or body is 54 micrograms (60×900=54000 ng).

Typical coating thicknesses and weights for DES, 3 mm in diameter and 20 mm in length, are 5 microns and 5 mg. Using a coating weight of 5 mg and oxide particle content of 54 micrograms, yields a volume fraction (by weight) of 1.08%, for a corrosion rate of 1000 ng/cm²/day. Using the maximum corrosion rates of 9500 ng/cm²/day, the maximum amount of metal particles, alloy particles, or metal oxide particles would be about 513 micrograms (54× 9.5=513 micrograms), yielding a maximum particle volume fraction (by weight) of 10.3%. Longer stents (up to 300 mm in length), used to treat vascular disease in superficial femoral arteries, and larger diameter stents (up to 40 mm in diameter), as those used in aortic stent grafts, have higher surface areas and could elute higher amounts of metallic corrosion products inside the body. Shorter and smaller diameter stents tend to cause lesser degradation products.

Based on these currently accepted rates of metal dissolution for commercially-available bare-metal stents implanted inside the body, the volume fraction of metal particles, alloy particles, and metal oxide particles is estimated to be in the range of approximately 1-10%, by weight, in the polymer coating. A lower amount of particles may be incorporated in the coating to reduce the impact on functional performance of the stent, drug-eluting stent, and endoprostheses, namely, the drug-release kinetics, polymer structure and properties, coating process, and coating performance. A higher amount of particles may be incorporated to impart more biohealing properties to the blood-contacting surface of the implanted device. One or more of metal particles, alloy particles, and metal oxide particles may be incorporated into polymers with volume fractions that range between approximately 0.001-20% by weight or range between approximately 0.0001-10%, by volume, depending on the density of the particles.

While the foregoing has been with reference to particular embodiments of the invention, it will be appreciated by those skilled in the art that changes in these embodiments may be made without departing from the principles and spirit of the invention.

What is claimed is:

1. An implantable device comprising:
   a stent made of a polymer;
   a drug in the polymer; and
   stainless steel particles distributed uniformly in the polymer in a volume fraction of approximately 0.0001 to 10%.

2. The implantable device of claim 1, wherein the stainless steel particles have a size of approximately 0.01 to 10,000 nm.

3. The implantable device of claim 1, wherein the polymer includes one or more of poly(acrylates), acrylic polymers, polycarbonates and copolymers, poly(cyanoacrylates), fluorinated polymers and copolymers, polycaprolactones, polylactides, polyglycolides, poly(D-lactides), poly(L-lactides), poly(D,L-lactides), poly(lactic acid), poly(glycolic acid), poly(lactide-co-glycolide)s, poly(glycolic acid-co-trimethylene carbonate)s, poly(lactic acid-co-trimethylene carbonate), poly-n-butyl methacrylate, polyethylene-co-vinyl acetate, poly-styrene-b-isobutylene-styrene, vinylidene fluoride, and hexafluoropropylene fluoropolymers, polyethylene glycol, hyaluronic acid, phosphorlycholine, poly(butylene succinate), polytetrafluoroethylene, polyesters, polyurethanes, poly(ethylene carbonate), poly(trimethylene carbonate), poly(trimethylcarbonate), polypropylene carbonate, poly(iminocarbonate), polyhydroxybutyrates, poly(hydroxybutyrate-co-valerate)s, polymers and copolymers of hydroxyl-ethyl-methacrylate, poly(methylmethacrylate), polydioxanones, polyorthoesters, polyanhydrides, polyphosphazenes, polyiminocarbonates, polytrimethylene carbonates and co-poly(ether-esters), poly(alkylene oxalates), polyurethanes, polyolefins, poly(isobutylene), vinyl halide polymers and copolymers, polyvinyl ethers, polyvinylidene halides, polyvinyl aromatics, polyvinyl esters, polyvinyl acetate, copolymers of vinyl monomers with each other and olefins, ethylene vinyl alcohol copolymers, polyamides, polyoxymethylenes, polyester amides, polyethers, poly(alkylene glycols), cellulose, and copolymers and combinations thereof.

4. An implantable device comprising:
a stent made of a polymer;
a drug in the polymer; and
cobalt-chromium alloy particles distributed uniformly in the polymer in a volume fraction of approximately 0.0001 to 5%.

5. The implantable device of claim 4, wherein the cobalt-chromium alloy particles have a size of approximately 0.01 to 10,000 nm.

6. The implantable device of claim 4, wherein the polymer includes one or more of poly(acrylates), acrylic polymers, polycarbonates and copolymers, poly(cyanoacrylates), fluorinated polymers and copolymers, polycaprolactones, polylactides, polyglycolides, poly(D-lactides), poly(L-lactides), poly(D,L-lactides), poly(lactic acid), poly(glycolic acid), poly(lactide-co-glycolide)s, poly(glycolic acid-co-trimethylene carbonate)s, poly(lactic acid-co-trimethylene carbonate), poly-n-butyl methacrylate, polyethylene-co-vinyl acetate, poly-styrene-b-isobutylene-styrene, vinylidene fluoride, and hexafluoropropylene fluoropolymers, polyethylene glycol, hyaluronic acid, phosphorlycholine, poly(butylene succinate), polytetrafluoroethylene, polyesters, polyurethanes, poly(ethylene carbonate), poly(trimethylene carbonate), poly(trimethylcarbonate), polypropylene carbonate, poly(iminocarbonate), polyhydroxybutyrates, poly(hydroxybutyrate-co-valerate)s, polymers and copolymers of hydroxyl-ethyl-methacrylate, poly(methylmethacrylate), polydioxanones, polyorthoesters, polyanhydrides, polyphosphazenes, polyiminocarbonates, polytrimethylene carbonates and co-poly(ether-esters), poly(alkylene oxalates), polyurethanes, polyolefins, poly(isobutylene), vinyl halide polymers and copolymers, polyvinyl ethers, polyvinylidene halides, polyvinyl aromatics, polyvinyl esters, polyvinyl acetate, copolymers of vinyl monomers with each other and olefins, ethylene vinyl alcohol copolymers, polyamides, polyoxymethylenes, polyester amides, polyethers, poly(alkylene glycols), cellulose, and copolymers and combinations thereof.

* * * * *